United States Patent [19]
Rosenberg et al.

[11] Patent Number: 5,677,161
[45] Date of Patent: *Oct. 14, 1997

[54] PREPARATION EXHIBITING ENZYMATIC ACTIVITY, A METHOD OF PRODUCING THE SAME, AND APPLICATIONS THEREOF

[75] Inventors: Eugene Rosenberg, Ramat Aviv; Yuval Shoham, Haifa, both of Israel

[73] Assignees: Korsnäs Aktiebolag, Gävle, Sweden; The Technion Research and Development Foundation Ltd., Haifa; Ramot-University Authority for Applied Research and Industrial Development Ltd., Tel Aviv, both of Israel

[*] Notice: The term of this patent shall not extend beyond the expiration date of Pat. No. 5,434,071.

[21] Appl. No.: 453,815

[22] Filed: May 30, 1995

Related U.S. Application Data

[63] Continuation of Ser. No. 63,551, May 18, 1993, Pat. No. 5,434,071, which is a continuation-in-part of Ser. No. 854,645, Sep. 2, 1992, abandoned.

[30] Foreign Application Priority Data

Jan. 10, 1990 [SE] Sweden ................................. 9000070

[51] Int. Cl.$^6$ .................................. C12N 9/24; C12N 9/26
[52] U.S. Cl. ........................ 435/200; 435/252.4; 435/278
[58] Field of Search .................................. 435/200, 252.4, 435/832, 278

[56] References Cited

U.S. PATENT DOCUMENTS 5,434,071  7/1995  Rosenberg et al. ..................... 435/200

*Primary Examiner*—Blaine Lankford
*Attorney, Agent, or Firm*—Bacon & Thomas

[57] ABSTRACT

The invention relates to a preparation exhibiting enzymatic activity, which preparation has the capability of delignifying wood pulp at a temperature of at least 65° C. and a pH of at least 9. Further, the invention relates to a method of producing said preparation by aerobically fermentating a selected *Bacillus stearothermophilus* strain. Furthermore, the invention relates to two isolated *Bacillus stearothermophilus* strains and mutants and variants thereof. The invention also relates to applications of the preparation of the invention, namely to a process comprising treatment of wood pulp with a preparation according to the invention, and a wood pulp and a fluff pulp treated with a preparation according to the invention, and also a paper, a board and a fluff made from a wood pulp treated with a preparation according to the invention.

11 Claims, No Drawings

5,677,161

PREPARATION EXHIBITING ENZYMATIC ACTIVITY, A METHOD OF PRODUCING THE SAME, AND APPLICATIONS THEREOF

This application is a continuation of U.S. application Ser. No. 08/063,551, filed May 18, 1993, now U.S. Pat. No. 5,434,071, which is a continuation-in-part of U.S. application Ser. No. 07/854,645, filed Sep. 2, 1992, abandoned.

SUMMARY OF THE INVENTION

The invention relates to a preparation exhibiting enzymatic activity, which preparation has the capability of delignifying wood pulp at a temperature of at least 65° C. and a pH of at least 9. Further, the invention relates to a method of producing said preparation by aerobically fermentating a selected *Bacillus stearothermophilus* strain. Furthermore, the invention relates to two isolated *Bacillus stearothermophilus* strains and mutants and variants thereof. The invention also relates to applications of the preparation of the invention, namely to a process comprising treatment of wood pulp with a preparation according to the invention, and a wood pulp and a fluff pulp treated with a preparation according to the invention, and also a paper, a board and a fluff made from a wood pulp treated with a preparation according to the invention.

BACKGROUND OF THE INVENTION

In the pulp and paper industry major efforts are made to reduce the use of chemicals in delignification and bleaching processes, since such chemicals, and especially organic chlorine compounds, in the effluent from bleach plants, give rise to environmental pollution.

One approach to reduce the use of chemicals in pulping and bleaching has been concerned with the use of lignin-degrading microorganisms. Lignin-degrading or lignin-modifying enzymes have also been suggested. A comprehensive review of lignin biodegradation has been published in Critical Reviews™ in *Biotechnology*, Vol. 6, Issue 1, 1987, pp. 1–60, Ed. Stewart, G. G. and Russell, I., CRC Press, Inc. Boca Raton, Fla.

Another approach has been concerned with removal of lignin by using hemicellulases to break hemicellulases bonds. A review article entitled "Hemicellulases: Their Occurrence, Purification, Properties, and Mode of Action," by Dekker, R. F. H. and Richards, G. N. has been published in *Advances in Carbohydrate Chemistry and Biochemistry*, Vol. 32, 1976, pp. 277–352.

Among the hemicellulases, xylanases are the ones that have attracted most attention for use in biopulping and biobleaching. FR 2 557 894-A1 discloses treatment of paper pulp with an enzymatic solution which does not have any cellulase activity and which contains xylanase. The treatment is effected at 20°–60° C., especially 40° C., and Example 6 reveals that the pH should be 5. However, the paper and pulp industry would be interested in treating wood pulp at higher temperatures and higher pHs for economical reasons and convenience, since some established bleaching processes are conducted at temperatures exceeding 65° C. and pH exceeding 9.

International patent publication number WO 91/18976 discloses α-L-arabinofuranosidase obtained from *B. stearo-thermophilus*. However, the molecular weight data for α-L-arabinofuranosidase is not disclosed and it would appear that different strains of *B. stearothermophilus* were used. More particularly, WO 91/18976 discloses the molecular weight ranges for xylanase obtained from *B stearothermophilus* as 18000–38000, whereas the molecular weight of the xylanase obtained by applicants is 41000 to 42000.

To our knowledge, no one has reported treatment of wood pulp with a preparation exhibiting enzymatic activity and having the capability of delignifying wood pulp at a temperature of at least 65° C. and a pH of at least 9.

DESCRIPTION OF THE INVENTION

The present invention provides a preparation exhibiting enzymatic activity, which preparation has the capability of delignifying wood pulp at a temperature of at least 65° C. and a pH of at least 9.

In the present specification and the appended claims, the expression "wood pulp" is to be interpreted broadly, and thus it is intended to comprise all kinds of lignocellulosic materials.

One aspect of the invention is directed to a preparation exhibiting enzymatic activity, which preparation is obtainable by aerobic fermentation, in a suitable medium, of a *Bacillus stearothermophilus* strain selected from the deposited strains NCIMB 40221 and NCIMB 40222 and mutants and variants thereof having substantially the same capability of producing said preparation as said strains NCIMB 40221 and NCIMB 40222, said preparation having the capability of delignifying wood pulp at a temperature of at least 65° C. and a pH of at least 9. In one embodiment of this aspect of the invention, the preparation is obtainable by aerobic fermentation, in a suitable medium comprising glucose as the carbon source, of a mutant strain of the *Bacillus stearo-thermophilus* strain NCIMB 40222. In another embodiment, the preparation is obtainable by aerobic fermentation, in a suitable medium comprising L-arabinose as the carbon source, of a mutant strain of the *B. stearothermophilus* strain NCIMB 40222.

In another embodiment the preparation according to the invention comprises an enzyme (xylanase) including the amino acid sequence I.D. No. (1):

—Lys—Asn—Ala—Asp—Ser—Tyr—Ala—Lys—Lys—Pro—His—Ile—Ser—Ala— (1)
—Leu—Asn—Ala—Pro—Gln—Leu—Asn—Gln—Arg—Tyr—Lys—Asn—Glu—
Phe—Thr—Ile—Gly—Ala—Ala—Val—Glu—Pro—Tyr—Gln—Leu—Gln—Asn— or a homologue thereof, the entire enzyme exhibiting enzymatic activity in a wood pulp medium. In this context, a homologue of said amino acid sequence is a homologous sequence having some amino acid substitutions, extensions or deletions which do not lead to the elimination of the enzymatic activity of the entire enzyme in a wood pulp medium. Further, a homologue of said amino acid sequence is any sequence which is sufficiently homologous on the nucleotide level to be recognized by any DNA or RNA probe derived from said sequence.

In another embodiment of the invention, the preparation according to the invention comprises an enzyme, α-L-arabinofuranosidase (AF), including the amino acid sequence I.D. No. (2)

—Ala—Thr—Lys—Lys—Ala—Thr—Met—Ile—Ile—Glu—Lys—Asp—Phe—Lys—Ile—Ala— (2)
Glu—Ile—Asp—Lys—Arg—Ile—Tyr—Gly—Ser—Phe—Ile—Glu—His—Leu—Gly—Arg—
Ala—Val—Tyr—Gly—Gly—Ile—Tyr—Glu—Pro—Gly—His—Pro—Gln—Ala—Asp—Glu—Asn—Gly— or a homologue thereof, the entire enzyme exhibit enzymatic activity in a wood pulp medium. (A homologue, in this context, of said amino acid sequence is a homologous sequence having some amino acid substitutions, extensions or deletions, which do not lead to the elimination of the enzymatic activity of the entire enzyme in a wood pulp medium. Further, a homologue of said amino acid sequence is any sequence which is sufficiently homologous on the nucleotide level to be recognized by any DNA or RNA probe derived from said sequence.)

In still another embodiment of this aspect of the invention, the preparation is a clarified culture broth. In yet another embodiment of this aspect of the invention, the preparation is a partially purified fraction of the culture broth exhibiting enzymatic activity in a wood pulp medium. The partially purified fraction is obtainable by ammonium sulphate precipitation. In a further embodiment of this aspect of the invention, the preparation is a highly purified fraction of the clarified culture broth which is obtainable by the use of a cation or anion exchanger, said fraction being in the form of a xylanase or an α-L-arabinofuranisodase exhibiting enzymatic activity in a wood pulp medium. In one particular embodiment, the xylanase has an approximate molecular weight between 41000 and 42000 Dalton determined by SDS PAGE and gel filtration and the following approximate amino acid composition determined as amino acid residues per molecule by amino acid analysis: Asx 58; Thr 12; Set 10; Glx 44; Pro 24; Gly 20; Ala 30; Cys 1; Val 28; Met 2; Ile 26; Leu 14; Tyr 22; Phe 16; Lys 38; His 6; Arg 12.

In another particular embodiment, the α-L-arabinofuranosidase has an approximate molecular weight of 128,000 and consists of two identical sub-units of 64,000 molecular weight (MW). (The native enzyme is of 128,000 MW as judged by SDS gel.)

Another aspect of the invention is directed to a method of producing a preparation exhibiting enzymatic activity, whereby a *Bacillus stearothermophilus* strain selected from the strains NCIMB 40221 and NCIMB 40222 and mutants and variants thereof having substantially the same capability of producing said preparation as said strains NCIMB 40221 and NCIMB 40222, is subjected to aerobic fermentation in a suitable medium, said preparation having the capability of delignifying wood pulp at a temperature of at least 65° C. and a pH of at least 9.

In a particular embodiment of the method according to the invention, a mutant strain of the *Bacillus stearothermophilus* strain NCIMB 40222 is subjected to aerobic fermentation in a suitable medium comprising glucose as the carbon source. In another embodiment of this aspect of the invention the fermentation broth is clarified, optionally by centrifugation. In yet another embodiment the clarified fermentation broth is subjected to ammonium sulphate precipitation, and optionally resuspension in a liquid medium, to yield a partially purified fraction of said clad fled culture broth exhibiting enzymatic activity in a wood pulp medium at a temperature of at least 65° C. and a pH of at least 9. In a further embodiment of the method according to the invention, the clarified fermentation broth is purified and concentrated using a cation exchanger, to yield a highly purified fraction in the form of a xylanase exhibiting enzymatic activity in a wood pulp medium at a temperature of at least 65° C. and a pH of at least 9.

In another particular embodiment of the method according to the invention, a strain of *Bacillus stearothermophilus* NCIMB 40222 is subjected to aerobic fermentation in a suitable medium comprising L-arabinose as the carbon source. The fermentation broth may be clarified, optionally by centrifugation. The clarified fermentation broth may be further subjected to precipitation, and optionally resuspension in a liquid medium, to yield a partially purified fraction of said clarified culture broth exhibiting enzymatic activity in a wood pulp medium at a temperature of at least 65° C. and a pH of at least 9. The clarified fermentation broth may be purified and concentrated using an anion exchanger, to yield a highly purified fraction in the form of α-L-arabinofuranosidase exhibiting enzymatic activity in a wood pulp medium at a temperature of at least 65° C. and a pH of at least 9.

Yet another aspect of the invention is directed to the isolated *Bacillus stearothermophilus* strains NCIMB 40221 and NCIMB 40222 and mutants and variants thereof, said mutants and variants having substantially the same capability of producing a preparation exhibiting enzymatic activity as said strains NCIMB 40221 and NCIMB 40222, said preparation having the capability of delignifying wood pulp at a temperature of at least 65° C. and a pH of at least 9.

Still another aspect of the invention is directed to a process comprising treatment of wood pulp, whereby wood pulp is treated in at least one step with a preparation according to the invention. In one embodiment of this aspect of the invention, the wood pulp to be treated is sulphate pulp. In another embodiment the sulphate pulp to be treated is a partially delignified sulphate pulp. In yet another embodiment of this aspect of the invention the partially delignified sulphate pulp to be treated is an oxygen-delignified sulphate pulp. The process comprising treatment of wood pulp is suitably effected at a temperature of at least 65° C. in a medium having a pH of at least 9.

An additional aspect of the invention is directed to products obtained from wood pulp which has been treated in at least one step with a preparation according to the invention. Thus, this aspect of the invention comprises wood pulp and fluff pulp which have been treated in at least one step with a preparation according to the invention, and paper, board and fluff that have been made from wood pulp which has been treated in at least one step with a preparation according to the invention.

A further aspect of the invention is directed to a DNA or RNA probe which recognizes the nucleotide sequence coding for the amino acid sequence I.D. No. (1), or which recognizes the nucleotide sequence coding for the amino acid sequence I.D. No. (2).

Additionally, one aspect of the invention is directed to an antibody which binds to the amino acid sequence I.D. No. (1), or to an antibody which binds to the amino acid sequence I.D. No. (2).

These last two aspects of the invention are useful in the finding of enzymes having the capability of delignifying wood pulp at a temperature of at least 65° C. and a pH of at least 9.

Isolation of Thermostable Enzyme Producing Organisms

The source of the organisms was water and mud samples taken from the water treatment pools at the pulp and paper mill of Korsnas, Gavle, Sweden. The enrichment medium (XM) contained 0.01% yeast extract, 0.04% tryptone and 0.2% xylan at pH 7.0. The same medium at pH 8.1 and 9.6 contained in addition $Na_2CO_3$. Water and mud samples were added to the XM media and were cultivated aerobically at 65° C. Samples from the cultures were transferred to fresh media every 2-3 days. Following 4 transfers, samples from the cultures were diluted and spread on XM agar plates (XM containing 2% agar).

Following three independent enrichment procedures, 30 strains were isolated that were able to grow on XM agar plates at 65° C. No isolates were obtained from the XM medium at pH 9.6. Out of the 30 isolates, 10 produced clear zones around the colony suggesting that they produce an extracellular xylanase. Two out of these ten isolates (strains T2 and T6) were selected for deposition.

Deposition of Microorganisms

Two strains, namely Bacillus sp T2 and Bacillus sp T6 were deposited under the Budapest Treaty at the National Collections of Industrial and Marine Bacteria Ltd. (NCIMB), Aberdeen, on Nov. 8, 1989. The accession numbers given were NCIMB 40221 and NCIMB 40222 for the strains T2 and T6, respectively.

Identification of Strains T2 and T6

The strains T2 and T6 are aerobic, gram positive, spore forming rods capable of growing at 65° C. These strains are considered to be different strains of *Bacillus stearothermophilus* by NCIMB, based on the following test results:

| Bacillus - second stage tests | | |
|---|---|---|
| Isolate No. | T2 (NCIMB 40221) | T6 (NCIMB 40222) |
| Tests at °C. | 60° C. | 60° C. |
| Spore shape[a] | E | E |
| Sporangium distended distinctly | – | – |
| Spore position dominant[b] | T | T |
| Anaerobic growth[c] | – | – |
| Growth in 5% NaCl | – | – |
| Growth in 7% NaCl | – | – |
| Growth in 10% NaCl | – | – |
| Growth in pH 5.7 broth | – | – |
| Acid from glucose[d] | – | – |
| Gas from glucose[d] | – | – |
| VP (acetonin) | – | – |
| Egg yolk agar opacity | No growth | No growth |
| Casein decomposition | + | + |
| Gelatin decomposition | + | (+) |
| Aesculin | + | – |
| Starch hydrolysis | +[R] | +[R] |
| $NO_3^-$ to $NO_2^-$ | – | – |
| Residual N | – | – |
| Citrate, Koser's | – | – |
| Dextrose azide | – | – |
| pH in VP broth | 5.5 | 6.3 |
| Litmus milk | | |
| coagulation | – | – |
| acidification | – | – |
| Catalase | + | + |
| Oxidase | + | + |

| Bacillus - second stage tests | | |
|---|---|---|
| Isolate No. | T2 (NCIMB 40221) | T6 (NCIMB 40222) |
| Growth temperatures °C. | | |
| 25° C. | – | – |
| 37° C. | – | – |
| 65° C. | + | + |
| 70° C. | – | – |

[a]E, ellopical or cylindrical; S, spherical or nearly so;
[b]C, central; T, terminal or subterminal; CT, central to terminal;
[c]On glucose agar;
[d]Peptone wate sugar, Andrade's indicator;
[R]restricted

Fatty Acids Composition of the Strains T2 and T6

The thermophilic xylanase positive isolates T2 and T6 were sent to Microbial ID, INC. Newark, Del., USA for fatty adds composition. The results received were as follows:

| Fatty acids composition (%) of xylanase positive thermophiles | | |
|---|---|---|
| Isolate: | T2 | T6 |
| Fatty acid | | |
| 9:0 | 0.73 | 0.64 |
| 12:0 | | 0.46 |
| 14:0 iso | | |
| 14:0 | 0.85 | 1.92 |
| 15:0 iso | 44.41 | 46.2 |
| 15: anteiso | 2.59 | 2.35 |
| 15:0 | | 0.53 |
| 16: iso | 6.25 | 4.15 |
| 16:1 | 4.24 | 5.53 |
| 16:0 | 5.29 | 6.14 |
| 17:1 iso H | 2.41 | 2.6 |
| 17:0 iso | 26.07 | 22.58 |
| 17:0 anteiso | 7.15 | 5.82 |
| 18:0 | | 1.09 |

Growth Characteristics of the Strains T2 and T6, and Preparation of Concentrated Crude Supernatants from the Cultured Strains Growth Media:

(1) XMP medium containing in g/liter: vitamine-free casamino acids, 4; yeast extract, 0.2; $MgSO_4$, 0.01; $(NH_4)_2SO_4$, 2; $K_2HPO_4$, 0.46; $KH_2PO_4$, 0.1; xylose, 5; MOPS (3-[N-morpholino]propane sulfonic acid), 10.4; and trace elements. The pH of the medium was 7.0.

(2) Basic salt medium (BSM) supplemented with 0.3% vitamin free casamino acids and 0.5% L-arabinose.

| The BSM contained, in grams/liter: | |
|---|---|
| $K_2PO_4.7H_2O$ | 0.75; |
| $KH_2PO_4$ | 0.15; |
| $MgSO_4.7H_2O$ | 0.1; |
| $(NH_4)SO_4$ | 2; |
| MOPS buffer (3-N-morpholino propane sulfonic acid) | 10.4; | and 1 ml of trace dement solution, which solution contained, in grams/liter:

| | |
|---|---|
| CaCl$_2$.2H$_2$O | 0.37; |
| CuSO$_4$.5H$_2$O | 0.62; |
| FeSO$_4$.7H$_2$O | 0.60; |
| MnSO$_4$.4H$_2$O | 0.59; |
| ZnSO$_4$.7H$_2$O | 0.42; |
| CoCl$_2$.6H$_2$O | 0.79; |
| Na$_2$MoO$_4$ | 0.696. |

The pH of the trace element solution was adjusted to 2.0 with sulfuric acid.

The pH of the BSM was adjusted to 7.0 and the carbon sources were added after sterilization. Growth was carried out in 125 ml flasks containing 25 ml medium and reciprocally shaking (180 strokes/min) in a water bath at 60° C.

Xylanase Activity

Xylanase activity was determined by incubating a fresh solution of xylan with extracellular supernatant fluid from media (1) and assaying for increase in reducing sugars by the ferricyanide method (Spiro, R. G. 1966, *Methods in Enzymology* 8: 7–9). Assay buffer was 50 mM Tris. Cl, pH 7.0 and 0.5% xylan (oat spelts, Sigma). Units of activity for xylanase are μmol reducing sugar generated per minute at 65° C.

Cell Turbidity of the Medium:

The cell turbidity of the medium is given in Klett units. 1KU=0.004 g of dry cell weight (DCW)/liter. Once the culture reaches its maximum density it tends to lyse as indicated by the sharp decrease of the culture turbidity.

The strains T2 and T6 were grown in XMP or BSM medium for 24 hours in a New Brunswick Microferm 7.5 liter fermentor. Growth was carried out in a working volume of 4 liter, at 60° C., agitation rate of 600 RPM and aeration rate of 7 liter per minute. Foaming was controlled automatically by adding silicon antifoam (5%, Fluka) and the working volume was maintained by adding sterile water. The initial starting inocula gave turbidities of 10KU (0.04 g DCW/liter). For the first 8 hours of the fermentations cell turbidity increased to 540 and 700 KU for strains T6 and T2, respectively. At 24 hours cell turbidity declined.

The culture liquid was cooled to room temperature and centrifuged (8000 g, 10 min., 20° C.) to remove the cells. The cell free supernatant contained 1.0–1.4 and 2.0–2.4 units xylanase per ml for strains T2 and T6 respectively and about 0.02 mg protein per ml for both strains. Protein was concentrated by adding to the supernatant solid ammonium sulfate to 80% saturation at 4° C. and centrifuging (9000 g, 15 min.) the mixture following 12 hours at 4° C. The precipitate was dissolved in a total volume of 100 ml of 10 mM phosphate buffer pH 7.0 and dialyzed three times against 5 liter of the same buffer at 4° C. The dialyzed solution (120 ml) contained about 7 mg/ml protein and 15–20 and 35–40 units of xylanase for strains T2 and T6 respectively.

| Time (h) | KU | Xylanase (U/ml) |
|---|---|---|
| Growth of strain T6 | | |
| 0 | 10 | nd |
| 2 | 25 | nd |
| 4 | 140 | nd |
| 6 | 400 | 1.48 |
| 8 | 540 | 1.88 |
| 11 | 540 | 1.78 |
| 14 | 528 | 2.26 |
| 24.5 | 280 | 2.42 |
| Growth of strain T2 | | |
| 0 | 10 | nd |
| 2 | 30 | nd |
| 4 | 160 | 0.75 |
| 6 | 430 | 0.58 |
| 8 | 700 | 0.98 |
| 11 | 600 | 1.05 |
| 24 | 250 | 1.28 |

It should be noted that the xylanase activity of the strains T2 and T6 did not decrease at the end of the fermentation.

The Preparation Exhibiting Enzymatic Activity According to the Invention

The cell-free supernatants from growth of the strains T2 and T6 in XMP medium contain at least one xylanase, since they were shown to exhibit xylanase activity. Said supernatants (also called crude enzyme preparations) and partially purified fractions thereof have been used in the treatment of unbleached and oxygen semi-bleached softwood sulphate pulps.

Unbleached and Oxygen Semi-bleached Pulp Samples

The pulp samples were softwood sulphate pulp samples taken from the Korsnäs mill.

The unbleached pulp sample was a sample taken after alkali digestion in a Kamyr digester, laboratory screened and washed, and said sample was dried over ight at 50° C. The semi-dry sample was used in the experiments, and it was designated K8. This material was dried at 105° C. to constant weight yielding a water content of 6.35%.

The oxygen semi-bleached pulp sample was a sample that had been treated in the Korsnäs fiber-line 3, and it was taken after the second oxygen treatment, laboratory screened and washed. A general description of the pulp treatment plant of Korsnäs has been published in Paper 26, September 1989, p. 20 and Nordisk Cellulosa 1989 No. 6, p. 8–11.

The oxygen semi-bleached pulp was designated K11.

Lignin Content of Pulps K8 and K11

The lignin contents of pulps K8 and K11 were determined by the procedure of The Swedish Association of Pulp and Paper Engineers, Series CCA5. The lignin content of K8 (unbleached) was 2.8% and the lignin content of K11 (oxygen semi-bleached) was 2.0%. Thus, the oxygen semi-bleached sample K11 had approximately 25% reduced value for lignin content compared to K8.

Experiments Conducted with Crude Enzyme Preparations from *Bacillus stearothermophilus* strains T2 and T6 on Delignification of Pulps K8 and K11

For the estimation of how much lignin is made extractable by the enzymatic preparations of the invention a sensitive spectrophotometric assay was used. The absorbance values at 350 nm ($\lambda_{350}$) were measured on the supernatant liquids of the samples, and measured values are presented as % lignin released.

The experiments and the results are summarized in Tables 1-5.

From the data given in the Tables 1-5 it can be concluded that the crude enzyme preparations from *Bacillus stereothermophilus* strains T2 and T6 are capable of delignifying both unbleached and semi-bleached pulp samples at pH values of at least 9 and at temperatures of at least 65° C. Moreover, it can be concluded that the % lignin released is both time- and concentration-dependent.

TABLE 1

Release of lignin from pulp K11 as a function of crude enzyme preparations from *B. stearothermophilus* strains T2 and T6[a]

| Enzyme | % lignin released[b] | |
|---|---|---|
| (mg/ml) | Total | Net |
| 0 | 8 | — |
| T2 (0.6) | 14 | 6 |
| T2 (0.8) | 17 | 9 |
| T2 (1.2) | 20 | 12 |
| T2 (1.9) | 22 | 14 |
| T6 (0.25) | 16 | 8 |
| T6 (0.5) | 18 | 10 |
| T6 (1.1) | 19 | 11 |

[a]The enzyme preparations were ammonium sulfate precipitate that were dissolved in 10 mM phosphate buffer, pH 9.0, to final concentrations of protein as indicated. The control was 10 mM phosphate buffer, pH 9.0. Pulp K11 was 150 mg in 3 ml.
[b]Incubation was for 18 h at 65° C. and pH 9.0. The % lignin released is based on $\lambda_{350}$ and is corrected for absorbance of the crude enzyme preparation at the appropriate concentration.

TABLE 2

Kinetics of lignin release from pulp K11 by crude enzyme preparation from *B. stearothermophilus* strains T2 and T6[a]

| | | % lignin released | |
|---|---|---|---|
| Time (h) | Enzyme[b] | Total | Net |
| 2 | T2 | 17 | 12 |
| 4 | T2 | 23 | 18 |
| 18 | T2 | 29 | 21 |
| 2 | T6 | 12 | 5 |
| 4 | T6 | 15 | 8 |
| 6 | T6 | 17 | 9 |
| 18 | T6 | 18 | 10 |

[a]The experiment was conducted as described in Table 1 at 65° C. and pH 9.0.
[b]The concentration of crude enzyme T2 and T6 were 2.8 and 1.5 mg protein/ml, respectively.

TABLE 3

Release of lignin as a function of temperature by crude enzyme preparations from *B. stearothermophilus* strains T2 and T6[a]

| Temperature | | % lignin released | |
|---|---|---|---|
| °C. | Enzyme[b] | Total | Net |
| 53 | T2 | 16 | 6 |
| 65 | T2 | 19 | 9 |
| 75 | T2 | 20 | 5 |
| 53 | T6 | 15 | 5 |
| 65 | T6 | 18 | 8 |
| 75 | T6 | 20 | 5 |

[a]The experiment was conducted as described in Table 1 at 65° C. and pH 9.0.
[b]The concentration of crude enzymes T2 and T6 were 1.7 and 0.7 mg protein/ml, respectively.

TABLE 4

Release of lignin from K11 as a function of pH[a].

| | | % lignon released | |
|---|---|---|---|
| pH | Enzyme[b] | Total | Net |
| 7 | T2 | 14 | 6.4 |
| 8 | T2 | 14 | 6.1 |
| 9 | T2 | 17 | 7.7 |
| 10 | T2 | 18 | 8.3 |
| 7 | T6 | 13 | 4 |
| 8 | T6 | 15 | 6 |
| 9 | T6 | 19 | 9 |
| 10 | T6 | 18 | 7 |
| 10.5 | T6 | 18 | 6 |

[a]The experiment was conducted as described in Table 1 at 65° C. and pH 9.0 for 18 h.
[b]The concentrations of crude enzyme preparations T2 and T6 were 1.7 and 1.5 mg protein/ml, respectively.

TABLE 5

Release of lignin from pulp K8[a]

| Enzyme preparation | Concentration (mg/ml) | % lignin released | |
|---|---|---|---|
| | | Total | Net |
| T2 | 0.8 | 16 | 5 |
| T2 | 1.2 | 17 | 6 |
| T2 | 1.6 | 20 | 9 |
| T6 | 0.3 | 14 | 3 |
| T6 | 0.6 | 15 | 4 |
| T6 | 1.1 | 17 | 6 |

[a]The experiment was conducted as described in Table 1 at 65° C. and pH 9.0 for 18 h, using pulp K8 instead of K11.

Preparation of a Highly Purified Fraction from Growth of Strain T6

A highly purified fraction (in the form of a xylanase) of the clarified culture broth from growth of strain T6 is obtainable by the use of a cation exchanger in a single concentration and purification step. Thus, xylanase T6 was purified and concentrated directly from the cell free supernatant by adsorption to the cation exchanger CM-52 (Whatman). However, with XMP medium, the recovery yield was only 21% presumably because of the high ionic strength of the medium. When the medium was dialysed against low ionic strength buffer or when MOPS was omitted from the medium the recovery yields were about 50%. To determine the minimal amount of CM-52 needed for effective adsorption from the clarified culture medium, different amounts of CM-52 were tested for purifying xylanase T6. The results are given in Table 6.

TABLE 6

Batch adsorption of xylanase T6 with different amounts of CM-52

| CM-52/broth (g/g) | Fraction | Volume (ml) | Xylanase (U/ml) | Total units | Yield (%) |
|---|---|---|---|---|---|
| | Supernatant | 100 | 0.78 | 78.0 | 100.0 |
| 0.1 | Extract | 40 | 1.04 | 41.6 | 53.3 |
| | Nonadsorbed | 100 | 0.055 | 5.5 | 7.0 |
| 0.05 | Extract | 30 | 1.3 | 39.9 | 50.0 |
| | Nonadsorbed | 100 | 0.077 | 7.7 | 9.8 |
| 0.02 | Extract | 15 | 1.94 | 29.1 | 37.3 |

TABLE 6-continued

Batch adsorption of xylanase T6 with different amounts of CM-52

| CM-52/broth (g/g) | Fraction | Volume (ml) | Xylanase (U/ml) | Total units | Yield (%) |
|---|---|---|---|---|---|
| | Nonadsorbed | 100 | 0.16 | 16.0 | 20.5 |
| 0.01 | Exftact | 14 | 2.05 | 28.7 | 36.8 |
| | Nonadsorbed | 100 | 0.24 | 24.0 | 30.8 |

As shown in Table 6, at 5% adsorbent the yield is 50%. Another commercially available cation exchanger is SE-52 (Whatman) (the negative groups are sulfoxyethyl attached to cellulose). SE-52 is known to have a larger adsorption capacity than CM-52. Since the purification step is also a concentrating step, it is advantageous to use as little adsorbent as possible. We therefore tried SE-52 for adsorbing xylanase. The results are given in Table 7.

TABLE 7

Batch adsorption of xylanase T6 with different amounts of SE-52

| SE-52/broth (g/g) | Fraction | Volume (ml) | Xylanase (U/ml) | Total units | Yield (%) |
|---|---|---|---|---|---|
| | Supernatant | 100 | 1.41 | 141.0 | 100.0 |
| 0.05 | Extract | 30 | 2.4 | 72.0 | 51.1 |
| 0.02 | Extract | 21 | 3.2 | 67.8 | 48.0 |
| 0.01 | Extract | 20 | 2.9 | 58.0 | 41.1 |

As shown in Table 7, only 2% of SE-52 was needed to obtain 48% recovery of xylanase T6.

Characterization of Xylanase T6

The molecular weight of xylanase T6 was determined by SDS PAGE and gel filtration, yielding values between 41,000 and 42,000 Daltons. The fact that both methods gave similar MW indicates that the enzyme is composed of a single polypeptide chain (SDS PAGE separates the protein subunits). The pI (the pH where the total charge of the protein is zero) of the enzyme was 9.0 determined by high voltage isoelectric focusing. The relatively high pI of the enzyme explains the positive charge of the enzyme at neutral pH. The pH optimum of the enzyme was around 7.0; at pH 9.0 the enzyme had about 50% of its pH 7.0 activity. The temperature profile of xylanase T6 activity is given in Table 8.

TABLE 8

The activity of xylanase T6 at different temperatures. *

| Temperature °C. | Relative Activity % |
|---|---|
| 45 | 28 |
| 55 | 51 |
| 60 | 70 |
| 65 | 81 |
| 70 | 92 |
| 75 | 100 |
| 80 | 73 |
| 85 | 40 |

* Reaction time: 5 minutes

The thermostability of xylanase T6 at a temperature of 65° C. and a pH of 9 is shown in Table 9.

TABLE 9

Thermostability of xylanase T6 at 65° C. and pH 9

| Time h | Relative activity % |
|---|---|
| 0 | 100 |
| 0.25 | 82 |
| 0.5 | 78 |
| 1 | 75 |
| 2 | 72 |
| 4 | 63 |

Additionally, it can be mentioned that at 65° C. and pH 7, no loss of activity was detected for over 10 h.

Obtaining Xylanase Constitutive Mutants from Strain T6

To obtain the mutants we used the fact that in many cases xylanase and xylosidase are under the same regulatory control (the same repressor). Strains that produced xylosidase can be easily detected on agar plates containing the chromogenic substrate p-nitrophenyl β-D-xylopyranoside (ONPX). Only constitutive mutants for xylosidase will produce yellow color on agar plates in the absence of xylose. To obtain xylosidase constitutive mutants, cells were mutagenized with MNNG (1-methyl-3-nitro-1-nitrosoguanidine) and then plated on agar plates containing ONPX without xylose. About one out of five hundred cells produced colonies which yielded yellow color on the agar plates. Thirty xylosidase constitutive mutants were isolated in this way, and all of them were also xylanase constitutives. The growth and xylanase production of two of these mutants (M-7 and M-28), growing in the presence of xylose or glucose, are given in Tables 10 and 11. On both media (XMP and GMP) the mutants exhibited similar growth rates. However, the mutants produced considerably higher levels of xylanase on XMP medium compared to T7. On GMP medium (glucose is the carbon source) strain T6 failed to produce detectable levels of xylanase whereas the mutants produced high level of xylanase activity. The xylanase from strain M-7 was purified and showed identical properties to the T6 xylanase.

TABLE 10

Growth and xylanase production of T6 xylanase constitutive mutants on XMP

| Strain | Time (h) | Turbidity (KU) | Xylanase (U/ml) |
|---|---|---|---|
| T6 | 0 | 10 | — |
| T6 | 2 | 40 | — |
| T6 | 4 | 150 | 0.5 |
| T6 | 6 | 200 | 0.8 |
| T6 | 12 | 310 | 2.1 |
| T6 | 24 | 290 | 2.3 |
| T6 | 30 | 270 | — |
| M7 | 0 | 10 | — |
| M7 | 2 | 30 | — |
| M7 | 4 | 190 | 0.9 |
| M7 | 6 | 270 | 1.6 |
| M7 | 12 | 350 | 2.1 |
| M7 | 24 | 310 | 2.3 |
| M7 | 30 | 310 | — |
| M28 | 0 | 20 | — |
| M28 | 1 | 20 | — |
| M28 | 4 | 40 | 0.6 |
| M28 | 6 | 120 | 2.0 |

TABLE 10-continued

Growth and xylanase production of T6 xylanase constitutive mutants on XMP

| Strain | Time (h) | Turbidity (KU) | Xylanase (U/ml) |
|---|---|---|---|
| M28 | 10 | 370 | 5.5 |
| M28 | 24 | 320 | 7.2 |

TABLE 11

Growth and xylanase production of T6 xylanase constitutive mutants on GMP

| Strain | Time (h) | Turbidity (KU) | Xylanase (U/ml) |
|---|---|---|---|
| T6 | 0 | 20 | — |
| T6 | 2 | 30 | 0 |
| T6 | 4 | 80 | 0.1 |
| T6 | 6 | 230 | 0.1 |
| T6 | 8 | 340 | 0.1 |
| T6 | 23 | 390 | 0.1 |
| T6 | 32 | 370 | — |
| M7 | 0 | 20 | — |
| M7 | 2 | 70 | 0.3 |
| M7 | 4 | 100 | 0.6 |
| M7 | 6 | 310 | 1.1 |
| M7 | 8 | 340 | 1.4 |
| M7 | 23 | 330 | 2.2 |
| M7 | 32 | 300 | — |
| M28 | 0 | 20 | — |
| M28 | 1 | 20 | — |
| M28 | 4 | 30 | 0.1 |
| M28 | 6 | 100 | 0.9 |
| M28 | 8 | 190 | 1.7 |
| M28 | 10 | 320 | 3.1 |
| M28 | 23 | 330 | 4.8 |

Fragment Sequence and Amino Acid Composition of Xylanase T-6

From a sufficiently long stretch of the N-terminal amino acid sequence of a protein, one can completely identify the protein. The sequence of one fragment of the xylanase T6 was determined twice at the Weizman Institute, Israel, on an Applied Biosystems gas phase microsequencer ABI 475A. The first protein sample was electroblotted first onto a PVDF membrane (Millipore) and gave only 20 amino acids. The second protein sample was purified first on a Superose 12 FPLC column (Pharmacia) and was sufficient for obtaining the sequence of 41 amino acids. The obtained sequence is sequence I.D. No. (1).

To further characterize the enzyme, an amino acid analysis was performed on the purified xylanase T6. The results from this analysis are shown in Table 12.

TABLE 12

Amino Acid composition of xylanase T6

| Pk Num | Ret Time | Component Name | Concentration (nmoles) | Residues per molecule[a] |
|---|---|---|---|---|
| 1 | 8.08 | Aspartic acid | 4.705 | 58 [b] |
| 2 | 9.76 | Threonine | 0.851 | 12 |
| 3 | 10.45 | Serine | 0.672 | 10 |
| 4 | 14.05 | Glutamic acid | 3.639 | 44 [c] |
| 5 | 15.52 | Proline | 1.950 | 24 |
| 6 | 18.80 | Glycine | 1.640 | 20 |

TABLE 12-continued

Amino Acid composition of xylanase T6

| Pk Num | Ret Time | Component Name | Concentration (nmoles) | Residues per molecule[a] |
|---|---|---|---|---|
| 7 | 19.84 | Alanine | 2.439 | 30 |
| 8 | 20.80 | Cystine | 0.061 | 1 |
| 9 | 21.81 | Valine | 2.250 | 28 |
| 10 | 23.60 | Methionine | 0.150 | 2 |
| 11 | 24.64 | Isoleucine | 2.064 | 26 |
| 12 | 25.39 | Leucine | 1.027 | 14 |
| 13 | 28.75 | Tyrosine | 1.613 | 22 |
| 14 | 29.87 | Phenylalanine | 1.269 | 16 |
| 15 | 38.37 | Lysine | 3.124 | 38 |
| 16 | 39.95 | Ammonia | 3.691 | |
| 17 | 42.65 | Histidine | 0.560 | 6 |
| 18 | 48.05 | Arginine | 0.904 | 12 |

[a] Based on a molecular weight of 42,000 Dalton; corrections were made for unstable amino acids.
[b] The aspartic acid is the sum of aspartic acid and asparagine (Asx)
[c] The glutamic acid is the sum of glumatic acid and glutamine (Glx).

Experiments Conducted with Enzyme on Pulp K14

The pulp sample K14 was an oxygen semi-bleached soft wood pulp from the Korsnäs mill. The enzyme was the purified thermophilic xylanase T6.

Various parameters effecting the extent of delignification of the pulp K14 were investigated.

The effect of fiber concentration is summarized in Table. 13.

TABLE 13

Effect of fiber concentration on xylanase treatment *

| Xylanase (U/ml) | Fiber (%) | Net Lignin Released (%) |
|---|---|---|
| 5.1 | 4.7 | 4.9 |
| 5.1 | 2.5 | 6.6 |
| 20.4 | 4.7 | 9.3 |
| 20.4 | 2.5 | 11.8 |
| 15.0 | 1.0 | 15.0 |
| 40.8 | 2.5 | 13.9 |
| 45.0 | 1.0 | 16.7 |

* Conditions: pH 9.0, 65° C., 2 h; K14 pulp: the no enzyme control was subtracted in each case.

As seen in Table 13, decreasing the fiber concentration from 4.7 to 2.5 to 1.0% dry weight fiber, enhanced the process. Since the enzymatic treatment is performed without mixing, it is likely that there was poor contact between the enzyme and insoluble substrate. For practical reasons, we chose to work at 2.5% fiber.

Effect of pH is given in Table 14.

TABLE 14

Effect of pH on xylanase treatment *

| pH | Buffer | Net Lignin Released (%) |
|---|---|---|
| 8.5 | 0.01M Phosphate | 8.3 |
| 9.0 | | 8.4 |
| 9.5 | | 6.3 |
| 8.5 | 0.1M Na$_2$SO$_4$ | 10.9 |
| 9.0 | | 10.2 |
| 9.5 | | 8.2 |

* Conditions: 2.5% K14 pulp, 15 U/ml xylanase, 2 h, 65° C.

As seen in Table 14, the enzyme is most effective at pH 8.5–9.0 in both potassium phosphate and sodium sulfate.

Earlier experiments indicated lower activities below pH 8.0 and above pH 9.5.

Effect of $Na_2SO_4$ concentration is shown in Table 15.

TABLE 15

Effect on $Na_2SO_4$ concentration *

| $Na_2SO_4$ (M) | Net Lignin Released (%) |
|---|---|
| 0 | 7.2 |
| 0.01 | 8.6 |
| 0.05 | 9.9 |
| 0.10 | 10.8 |
| 0.15 | 11.5 |
| 0.20 | 10.7 |

* Conditions: 2.5% K14 pulp, 10 U/ml xylanase, pH 9.0, 65° C., 2 h.

The treatment was effective from no added $Na_2SO_4$ up to 0.2M with optimum activity at 0.15M $Na_2SO_4$.

Effect of xylanase concentration is summarized in Table 16.

TABLE 16

Release of lignin as a function of xylanase concentration*

| Xylanase (U/ml) | Buffer | Lignin Release (% Klason) |
|---|---|---|
| 0 | 0.01M K Phosphate | 0 |
| 5 | | 8 |
| 10 | | 10 |
| 15 | | 12 |
| 45 | | 14 |
| 0 | 0.1M $Na_2SO_4$ | 0 |
| 5 | | 12 |
| 10 | | 13 |
| 15 | | 14 |
| 45 | | 16 |

*Conditions: 2.5% dry fiber K14, 2 h, pH 9, 65° C.

As seen in Table 16, there was a concentration dependent release of lignin up to approximately 15 U/ml in both 0.1M $Na_2SO_4$ and potassium phosphate buffer. Higher concentrations of enzyme or a longer period of incubation (4 h) increased the net lignin released only slightly.

Preparation of 10 g and 50 g Samples of Treated K14 for Further Tests 10 g samples of K14 pulp were treated with 15 U/ml and 45 U/ml xylanase for 2 h and 4 h, together with the appropriate controls. All samples were prepared in duplicate. All incubations were carried out 9.0 and 65° C. The spectrophotometric analysis of lignin release is shown in Tables 17 (phosphate buffer) and 18 (0.1M $Na_2SO_4$). The net release of lignin ranged from 10.3 to 14.9%, with the 45 U/ml enzyme and 4 h incubation periods giving slightly higher values than 15 U/ml and 2 h.

Recently, 50 g samples of pulp were treated in duplicate for additional analyses. The net release of lignin was 10.8% for 15 U/ml enzyme for 2h and 12.6% for 15 U/ml for 4 h.

TABLE 17

Xylanase treatment of 10 g K14 pulp in phosphate buffer*

| Xylanase | Time | Lignin Released % | |
|---|---|---|---|
| (U/ml) | (h) | Total | Net |
| 0 | 2 | 5.3 | 0 |
| 15 | 2 | 15.6 | 10.3 |
| 45 | 2 | 17.9 | 12.6 |
| 0 | 4 | 6.3 | 0 |
| 15 | 4 | 17.4 | 11.1 |
| 45 | 4 | 20.1 | 13.8 |

*Conditions: 2.5% K14 pulp, pH 9.5, 65° C.; average of two experiments

TABLE 18

Xylanase treatment of 10 g K14 pulp in 0.1M $Na_2SO_4$

| Xylanase | Time | Lignin Released (%) | |
|---|---|---|---|
| (U/ml) | (h) | Total | Net |
| 0 | 2 | 5.9 | 0 |
| 15 | 2 | 17.6 | 11.7 |
| 45 | 2 | 19.8 | 13.9 |
| 0 | 4 | 7.0 | 0 |
| 15 | 4 | 19.4 | 12.4 |
| 45 | 4 | 21.9 | 14.9 |

*Conditions: As in Table 17

Analysis of Xylanase-treated 10 g Samples

The results of the analyses are summarized in Tables 19–23. The parameters given in the tables were according to the SCAN Test series, except for the Zero-span values which were measured according to the manufacturers (Pulmac Instruments, Ltd., Canada) instructions. Table 19 presents the data obtained using pulp that had been treated for 2 h at 65° C., pH 9.0, in 0.1M $Na_2SO_4$ with no enzyme (control) and 15 U/ml enzyme. As can be seen, there was excellent reproducibility with the duplicate samples, prepared at two week intervals. The largest effect was on pentosan content, which decreased 17.4%. There were small but significant decreases in Kappa number and tensile indices, and increases in brightness, viscosity and zero-span values.

The values of the above properties for the pulp or handsheets made from the pulp were not very different at 15 U/ml and 45 U/ml enzyme, 2 h and 4 h treatment and use of 0.01M potassium phosphate and 0.1M $Na_2SO_4$ (Tables 20 and 21).

To analyze the significance of these data, the values of pulp and paper properties are presented in Tables 22 and 23 as percent changes compared to the appropriate controls. The conclusions are as follows:

1. Pentosans are partially removed (10.4–22.2%); higher levels of enzyme remove more pentosans.
2. There is a small but significant increase in viscosity; this can be explained by the removal of pentosans (about 1% of the dry weight of K14). There is no evidence for cellulose degradation, even at the highest concentration of enzyme at 4 h at 65° C., pH 9.
3. The Kappa number decreased in all eight conditions examined (range: 5.5–9.1%). Since the values did not decrease further at higher enzyme concentrations (whereas pentosans were), the higher levels of enzyme appeared to remove pentosans that were not linked to lignin.

4. In all eight conditions tested, the handsheets showed small increases in brightness and zero-span values and decreases in tensile indices.

TABLE 19

Xylanase treatment of K14 pulp*

| Parameter | Control | | Enzyme treated | | Average Change | (5) |
|---|---|---|---|---|---|---|
| Kappa No. | 17.3 | 16.8 | 16.0 | 15.5 | −7.6 | (±0.1) |
| Viscosity (dm³/Kg) | 1066 | 1045 | 1072 | 1059 | +0.8 | (±0.1) |
| Pentosan (%) | 9.1 | 9.3 | 7.7 | 7.5 | −17.4 | (±1.8) |
| Handsheets (75 g/m²) | | | | | | |
| Brightness (% ISO) | 32.5 | 32.8 | 33.4 | 33.8 | +2.9 | (±0.1) |
| Tensile Index (Nm/g) | 20.9 | 20.4 | 19.0 | 19.3 | −7.2 | (±1.8) |
| Zero-span (Wet), (Nm/g) | 95.2 | 97.8 | 101.5 | 104.3 | +6.3 | (±0.3) |

*Conditions: 15 U/ml enzyme, pH 9.0, 2 h, 0.1M Na₂SO₄

TABLE 20

Xylanase treatment of K14 pulp in 0.1M Na₂SO₄*

| Parameter | 0/ml 2 h | 15 U/ml 2 h | 45 U/ml 2 h | 0 U/ml 4 h | 15 U/ml 4 h | 45 U/ml 4 h |
|---|---|---|---|---|---|---|
| Kappa | 17.1 | 15.8 | 16.0 | 17.0 | 15.4 | 15.8 |
| Viscosity | 1055 | 1066 | 1072 | 1061 | 1075 | 1075 |
| Pentosan | 9.2 | 7.6 | 7.3 | 9.0 | 7.5 | 7.0 |
| Brightness | 32.6 | 33.6 | 34.1 | 32.6 | 34.1 | 34.4 |
| Tensile | 20.7 | 19.2 | 20.7 | 21.2 | 19.6 | 19.8 |
| Zero-span | 97 | 103 | 104 | 100 | 104 | 103 |

*Average of two experiments; conditions as in Table 19.

TABLE 21

Xylanase treatment of K14 pulp in 0.01 phosphate buffer*

| Parameter | 0/ml 2 h | 15 U/ml 2 h | 45 U/ml 2 h | 0 U/ml 4 h | 15 U/ml 4 h | 45 U/ml 4 h |
|---|---|---|---|---|---|---|
| Kappa | 17.0 | 15.9 | 16.0 | 17.2 | 16.0 | 16.2 |
| Viscosity | 1065 | 1073 | 1076 | 1060 | 1070 | 1073 |
| Pentosan | 91 | 8.2 | 7.4 | 9.0 | 7.9 | 7.4 |
| Brightness | 31.8 | 33.2 | 33.6 | 32.6 | 33.2 | 33.7 |
| Tensile | 21.0 | 19.2 | 20.4 | 20.9 | 19.4 | 20.3 |
| Zero-span | 101 | 101 | 107 | 99 | 102 | 104. |

*Average of two experiments.

TABLE 22

Xylanase treatment of K14 pulp*

Change (%)

| Parameter | 15 U/ml 2 h | 15 U/ml 4 h | 45 U/ml 2 h | 45 U/ml 4 h |
|---|---|---|---|---|
| Kappa | −7.6 | −9.1 | −5.9 | −7.1 |
| Viscosity | +0.8 | +1.4 | +1.5 | +1.4 |
| Pentosan | −17.4 | −16.5 | −20.6 | −22.2 |
| Brightness | +2.9 | +4.4 | +4.7 | +5.3 |
| Tensile | −7.2 | −7.5 | −6.8 | −6.4 |
| Zero-span | +6.3 | +3.7 | +7.1 | +3.0 |

*0.1M Na₂SO₄; Data from Table 20

TABLE 23

Xylanase treatment of K14 pulp*

Change (%)

| Parameter | 15 U/ml 2 h | 15 U/ml 4 h | 45 U/ml 2 h | 45 U/ml 4 h |
|---|---|---|---|---|
| Kappa | −7.3 | −7.0 | −6.7 | −5.5 |
| Viscosity | +0.8 | +0.9 | +1.0 | +1.2 |
| Pentosan | −10.4 | −12.7 | −20.7 | −18.4 |
| Brightness | +4.3 | +2.8 | +5.3 | +3.2 |
| Tensile | −8.8 | −7.4 | −3.3 | −2.9 |
| Zero-span | −0.7 | +8.3 | +5.8 | +5.2 |

*0.01M phosphate; Data from Table 21

Test of Bleachability

The pulp K14 with Kappa number 18.5 was used to test the effect of enzyme treatment on bleachability. The pulp K14 was exposed to enzyme treatment at a concentration of 15 units/ml of xylanase produced from the strain T6. After the enzymatic treatment the pulp was bleached with the bleaching sequence used in the Korsnäs mill: Chlorine dioxide (D0)—Alkali extraction reinforced with oxygen (EO)—Chlorine dioxide (D1)—Chlorine dioxide (D2).

The enzymatic treatment reduced the lignin content of the pulp to a Kappa number of 15.9. A pulp treated in the same way as the enzyme treated pulp, i.e. at 65° C. and pH 9 in 100 mM Na₂SO₄ buffer, but without addition of enzymes, was delignified to a Kappa number of 17.2. The net effect of the enzymatic treatment was a delignification from Kappa number 17.,2 to 15.9, i.e., a delignification of 8%.

The pulp treated with enzymes in the sulfate buffer system consumed 47 kg chlorine dioxide (active chlorine)/ton of pulp when bleaching to an ISO-brightness of 83% with the bleaching sequence D0(E0)D1D2. The corresponding consumption for the pulp treated merely with buffer solution was 59 kg chlorine dioxide (a C1)/ton of pulp, i.e. the enzyme treated pulp consumed 20% less chlorine dioxide.

Fragment Sequence and Amino Acid Composition of α-L-arabinofuranosidase

The N-terminal sequence of α-L-arabinofuranosidase (AF) was done on an Applied Biosystems model 475A gas phase sequencer. The AF was purified by the following procedure. The cell-free broth was concentrated against solid PEG 20,000. The sample was then applied on an anion exchanger (mono Q HR 5/5, Pharmacia). Fractions with activity were pooled together, concentrated and then applied on a gel filtration column (Superose 12 HR 10/30). The active fractions contained AF that was over 99% clean as judged by SDS-PAGE and contained 500 U/mg. This material was concentrated (0.5 mg/ml) and was used for the N-terminal sequencing. AF from T6 consists of 2 identical sub-units of 64,000 molecular weight (the native enzyme is of 128,00 MW as judged by SDS gel). The pI of AF from T6 is about 4.5.

The N-terminal sequence is sequence I.D. No. (2).

Bleaching Experiments

The bleaching experiments using AF from T6 were conducted in the same way as above for xylanase. The results are given in Tables 24–26 as follows.

TABLE 24

The effect of pH at AF enzyme concentration of 20 U/ml and Temp. 65° C.

| pH | % lignin released | |
|---|---|---|
| | Total | Net |
| 7.0 | 16.1 | 2.9 |
| 8.0 | 15 | 2.3 |
| 9.0 | 15.5 | 1.2 |

TABLE 25

The effect of AF enzyme concentration at pH 9.0 and Temp. 65° C.

| Enzyme | % lignin released | |
|---|---|---|
| U/ml | Total | Net |
| 20 | 15.5 | 1.2 |
| 40 | 16.4 | 2.4 |
| 60 | 16.5 | 2.5 |

TABLE 26

Bleaching with AF together with xylanase at pH 9.0 and Temp 65° C.

| Treatment | % lignin released | |
|---|---|---|
| | Total | Net |
| Xylanase (U/ml) | 22.1 | 9.2 |
| AF (40 U/ml) | 16.4 | 2.4 |
| Xylanase + AF | 27.8 | 13.5 |

As shown in Table 26, the preparation exhibiting xylanase activity and α-L-arabinofuranosidase activity shows more bleaching than the sum of each enzyme above and thus, the xylanase and α-L-arabinofuranosidase have a synergistic effect in delignifying wood pulp at a temperature of at least 65° C. and a pH of at least 9.

The invention includes a preparation exhibiting xylanase activity and α-L-arabinofuranosidase activity which comprises purified xylanase and purified α-L-arabinofuranosidase, each separately having the capability of delignifying wood pulp at a temperature of at least 65° C. and a pH of at least 9, said preparation having the capability of synergistically delignifying wood pulp at a temperature of at lesat 65° C. and a pH of at least 9. The components exhibiting xylanase and α-L-arabinofuranosidase activity are obtained by aerobic fermentation in a suitable medium of B. stearothermophilus strains NCIMB 40221 and NCIMB 40222 and mutants and variants thereof, said mutants and variants having substantially the same capability of producing a preparation exhibiting said xylanase activity and said α-L-arabinofuranosidase activity as said strains NCIMB 40221 and NCIMB 40222.

We claim:

1. Process comprising delignification of wood pulp, wherein said wood pulp is treated in at least one step with a composition comprising an enzyme which is capable of delignification at a temperature of at least 65° C. and a pH of at least 9, said composition produced by *Bacillus stearothermophilus* strain NCIMB 40221, strain NCIMB 40222, or a mutant thereof.

2. A process according to claim 1, wherein said wood pulp is sulphate pulp.

3. A process according to claim 2, wherein said sulphate pulp is a partially delignified sulphate pulp.

4. A process according to claim 3, wherein said partially delignified sulphate pulp is an oxygen-delignified sulphate pulp.

5. A process according to claim 1, wherein said treatment is effected at a temperature of at least 65° C. in a medium having a pH of at least 9.

6. The process of claim 1, wherein the *Bacillus stearothermophilus* is a mutant of strain NCIMB 40221 or NCIMB 40222 and is capable of growing on glucose as a carbon source.

7. An enzymatic composition for delignifying wood pulp, which is capable of delignification at a temperature of at least 65° C. and pH of at least 9, said composition comprising xylanase, said composition produced by a process of aerobically fermenting *Bacillus stearothermophilus* strain NCIMB 40221, strain NCIMB 40222, or a mutant thereof, in a culture medium and recovering said enzymatic composition, said xylanase having an isoelectric point of 9.0 determined by isoelectric focusing, an approximate molecular weight between 41000 and 42000 Dalton determined by SDS PAGE, and having the partial N-terminal amino acid sequence -Lys-Asn-Ala-Asp-Ser-Tyr-Ala-Lys-Lys-Pro-His-Ile-Ser-Ala-Leu-Asn-Ala-Pro-Gln-Leu-Asn-Gln-Arg-Tyr-Ile-Asn-Glu-Phe-Thr-Ile-Gly-Ala-Ala-Val-Glu-Pro-Tyr-Gln-Leu-Gln-Asn-.

8. The composition of claim 7 which is substantially pure xylanase.

9. The enzymatic composition of claim 7, wherein the culture medium used in the process of preparing the preparation contains glucose.

10. The enzymatic composition of claim 7, wherein the *Bacillus stearothermophilus* is a mutant of strain NCIMB 40222.

11. The enzymatic composition of claim 7, wherein the *Bacillus stearothermophilus* is a mutant of strain NCIMB 40221 or 40222 and is capable of growing on glucose as a carbon source.

* * * * *